United States Patent [19]

Lee

[11] Patent Number: 4,722,749
[45] Date of Patent: Feb. 2, 1988

[54] PYRIDINESULFONAMIDES AND THEIR USE AS HERBICIDAL AGENTS

[75] Inventor: Shy-Fuh Lee, Sunnyvale, Calif.

[73] Assignee: Sandoz Ltd., Basel, Switzerland

[21] Appl. No.: 938,681

[22] Filed: Dec. 5, 1986

Related U.S. Application Data

[63] Continuation-in-part of Ser. No. 879,658, Jun. 27, 1986, abandoned, which is a continuation-in-part of Ser. No. 812,088, Dec. 23, 1985, abandoned.

[51] Int. Cl.$^4$ .................. A01N 43/40; C07D 213/02
[52] U.S. Cl. ........................................ 71/94; 546/293; 546/261; 546/264; 544/238; 544/239; 544/240

[58] Field of Search ............................ 546/293; 71/94

[56] References Cited

FOREIGN PATENT DOCUMENTS 048733  3/1971  Japan ................................. 546/293

*Primary Examiner*—Henry R. Jiles
*Assistant Examiner*—J. Richter
*Attorney, Agent, or Firm*—Jacqueline S. Larson

[57] ABSTRACT

Substituted 2-pyridinesulfonamide 1-oxides, synthesis thereof, intermediates therefor, and the use of said compounds for the control of weeds.

19 Claims, No Drawings

PYRIDINESULFONAMIDES AND THEIR USE AS HERBICIDAL AGENTS

This is a continuation-in-part of Ser. No. 879,658 filed June 27, 1986, now abandoned which is a continuation-in-part of Ser. No. 812,088 filed Dec. 23, 1985 now abandoned.

This invention relates to substituted 2-pyridinesulfonamide 1-oxides, synthesis thereof, intermediates therefor, and the use of the compounds for the control of weeds.

More particularly, the compounds of the present invention are represented by the following formula (A):

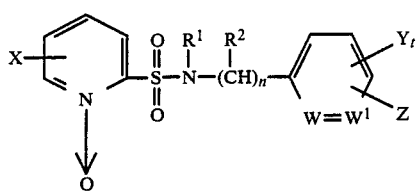

wherein
n is zero or one;
t is zero, one, two, three or four;
$R^1$ is hydrogen, unsubstituted or halogenated $C_{1-8}$alkyl, unsubstituted or halogenated $C_{2-8}$alkenyl, $C_{2-8}$alkynyl, $C_{2-10}$alkoxyalkyl or $C_{2-10}$alkylthioalkyl;
$R^2$ is hydrogen or $C_{1-8}$alkyl;
W is CH or N;
$W^1$ is CH or N; wherein when either of W or $W^1$ is CH, it can be independently substituted by Y or Z;
X is hydrogen, unsubstituted or halogenated $C_{1-8}$alkyl, $C_{1-8}$alkoxy or halogen;
Y is unsubstituted or halogenated $C_{1-8}$alkyl, unsubstituted or halogenated $C_{1-8}$alkoxy, $C_{1-8}$alkylthio, $C_{2-8}$alkoxycarbonyl, nitro, cyano or halogen; and
Z is hydrogen or independently selected from the values of Y.

In practice of the present invention, n is preferably zero or one, more preferably zero.

t is preferably zero, one, two or three; more preferably zero, one or two; most preferably zero or one.

Where any of the substituents $R^1$, $R^2$, X, Y or Z is or comprises halogen, such halogen is conveniently selected from bromo, chloro and fluoro.

Where $R^1$ is unsubstituted or halogenated $C_{1-8}$alkyl, such alkyl has preferably 1 to 5, more preferably 1 to 3 C atoms.

Where $R^1$ is unsubstituted or halogenated $C_{2-8}$alkenyl, such alkenyl has e.g. 3 to 5, preferably 3 or 4 C-atoms.

Where $R^1$ is alkynyl it comprises e.g. 3 to 5, preferably 3 C-atoms.

Where $R^1$ is halogenated $C_{1-8}$alkyl or $C_{2-8}$alkenyl, it comprises preferably 1 to 3, e.g. 1 or 2 halogen atoms.

Where $R^1$ is $C_{2-10}$alkoxyalkyl, it is preferably $C_{1-5}$alkoxy-$C_{1-5}$alkyl, e.g. $CH_2OCH_3$.

Where $R^1$ is $C_{2-10}$alkylthioalkyl, it is preferably $C_{1-5}$alkylthio-$C_{1-5}$alkyl.

Where $R^2$ is $C_{1-8}$alkyl it has preferably 1 to 5 C-atoms.

Where X is unsubstituted or halogenated $C_{1-8}$alkyl, it comprises preferably 1 to 5, e.g. 1 C-atom.

Where X is halogenated $C_{1-8}$alkyl it comprises preferably from 1 to 3 halogens. An example of a preferred haloalkyl significance of X is $CF_3$.

Where X is $C_{1-8}$alkoxy it has preferably from 1 to 5 C-atoms.

Where any of Y and Z is unsubstituted or halogenated $C_{1-8}$alkyl, it comprises preferably from 1 to 5, more preferably 1 or 2 C-atoms.

Where any of Y and Z is halogenated $C_{1-8}$alkyl, it comprises preferably from 1 to 3 halogens.

An example of a preferred haloalkyl significance of Y or Z is $CF_3$.

Where any of Y and Z is unsubstituted or halogenated $C_{1-8}$alkoxy it comprises preferably from 1 to 5, particularly 1 or 2 carbon atoms.

Where any of Y and Z is halogenated $C_{1-8}$alkoxy it comprises preferably from 1 to 4 halogen atoms.

Where any of Y and Z is $C_{1-8}$alkylthio, it comprises preferably from 1 to 5 C-atoms.

Where any of Y and Z is halogen, it is preferably F or Cl.

Where any of Y and Z is $C_{2-8}$alkoxycarbonyl, it is preferably ($C_{1-5}$alkoxy)carbonyl.

$R^1$ is preferably $C_{1-5}$alkyl, $C_{2-5}$alkenyl or $C_{2-5}$alkynyl.
$R^2$ is preferably hydrogen.
X is preferably hydrogen or halogen.
Y is preferably $C_{1-5}$alkyl, $CF_3$, nitro or halogen.
Z is preferably $C_{1-5}$alkyl, $CF_3$, halogen, or di- or trifluorinated $C_{1-5}$alkoxy.

It is preferred that at least one of W and $W^1$ is CH; more preferably W and $W^1$ are both CH.

A preferred sub-group of the present invention is represented by the following formula (A')

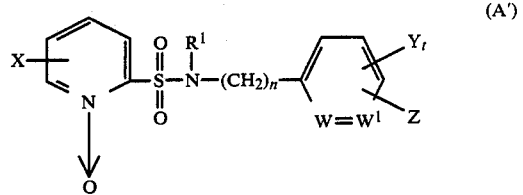

wherein
n is zero or one;
t is zero or one;
$R^1$ is $C_{1-5}$alkyl, $C_{3-5}$alkenyl, mono- or dihalogenated $C_{3-5}$alkenyl $C_{3-5}$alkynyl or $C_{1-5}$alkoxy-$C_{1-5}$alkyl;
one of W and $W^1$ is CH and the other of W and $W^1$ is CH or N;
wherein when either of W or $W^1$ is CH, it can be independently substituted by Y or Z;
X is hydrogen, $C_{1-5}$alkyl or halogen;
Y is $C_{1-5}$alkyl, halogen, $CF_3$, or di- or trihalogenated $C_{1-5}$alkoxy; and
Z is hydrogen; $C_{1-5}$alkyl; halogen; $CF_3$; di-, tri or tetrahalogenated $C_{1-5}$-alkoxy; ($C_{1-5}$alkoxy)carbonyl; CN; or $NO_2$.

A particularly preferred sub-group within the class of the compounds of the present invention of formula A' is one in which n is zero, t is zero, $R^1$ is methyl or ethyl, each of W and $W^1$ is CH, X is hydrogen, chloro or fluoro in the 5-position, and Z is in the 2-position and is fluoro, trifluoromethyl, difluoromethoxy or 2,2,2-trifluoroethoxy.

Another particularly preferred sub-group of compounds of formula A' is one in which n is zero, t is one, $R^1$ is methyl or ethyl, each of W and $W^1$ is CH, X is hydrogen, chloro or fluoro in the 5-position, Y is chloro or fluoro, and Z is in the 2-position and is fluoro, trifluoromethyl, difluoromethoxy or 2,2,2-trifluoroethoxy.

The invention also comprises processes of preparing a compound of formula A, comprising:

(a) N-oxidizing the 2-pyridylsulfonyl group of a compound of formula I

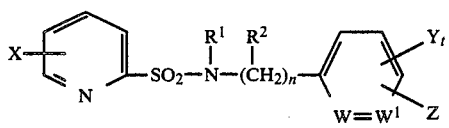

where X, $R^1$, $R^2$, n, W, $W^1$, Z, Y and t are as defined above, with an oxidizing agent, followed, where desired, by N-alkylating a thus obtained compound of formula A wherein $R^1$ is H with a compound of formula II

wherein $R^1_a$ is unsubstituted or halogenated $C_{1-8}$alkyl, unsubstituted or halogenated $C_{2-8}$alkenyl, $C_{2-8}$alkynyl, $C_{2-10}$alkoxyalkyl or $C_{2-10}$alkylthioalkyl, and Hal is halogen, or a reactive functional derivative of a compound of formula II; or (b) N-sulfonating an amine of formula III

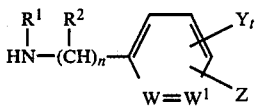

wherein $R^1$, $R^2$, n, W, $W^1$, Z, Y and t are as defined above, with a compound of formula IV

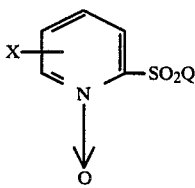

where X is as defined above, and Q is halogen, followed, where desired, by N-alkylating a thus obtained compound of formula A wherein $R^1$ is H with a compound of formula II

where $R^1_a$ and Hal are as defined above, or a reactive functional derivative of a compound of formula II.

The N-oxidation of the 2-pyridylsulfonyl group of a compound of formula I (process a) may be carried out according to processes and conditions known in the art of oxidation of pyridine compounds. A suitable oxidizing agent is peracetic acid, for example in the form of the commercially available aqueous 40% solution. A suitable reaction temperature is room temperature or moderately above, e.g. 20° to 50° C.

The reaction of formulae III & IV (process b) may be effected under the conditions known for the preparation of sulfonamides starting from the corresponding sulfonyl halides and amines. The reaction is conveniently carried out in a solvent which is inert under the reaction conditions, such as methylene chloride or benzene. A suitable reaction temperature is room temperature or below, e.g. −10° to 20° C.

The optional N-alkylation of a compound of formula A where $R^1$ is H may be carried out under processes and conditions known in the art of alkylation of amino compounds. In the process, compound A is preferably as a salt, e.g. the sodium salt (i.e. $R^1$ is Na).

The compounds of formula A may be recovered from the reaction mixture in which they are formed by working up by established procedures.

The starting materials are known or, in cases where they are novel, can be produced and purified in accordance with known processes or in a manner analogous to processes described herein or to known processes.

The novel compounds of formula A are useful as herbicides for the control of weed plants, using pre- and/or postemergent treatments. "Herbicide", as used herein, refers to an active ingredient which modifies the growth of plants because of phytotoxic or plant growth regulating properties so as to retard the growth of the plant or to damage the plant sufficiently to kill it. By "plants" it is meant germinating seeds, emerging seedlings and established vegetation including underground portions. While some activity is shown when weeds are treated postemergence, the compounds of the present invention generally are more effective when used as preemergent herbicides. Application of a compound of the present invention is made according to conventional procedure to the weed or its locus using an herbicidally effective amount of the compound, usually from about one-half or less to ten pounds per acre. The application of a compound of the present invention to the "locus" of the weed plant includes application to the seeds, the plant or parts of the plant, or the soil.

While the compounds of formula A have activity on broadleaf (dicotyledoneous) plants, the compounds in general demonstrate a higher level of herbicidal activity on the grassy (monocotyledoneous) plants and the sedges when applied pre- or postemergence, as shown by greenhouse tests with test dosages equivalent to an application rate of from 0.03 to 10 kg/ha after pre- or postemergence application. Particularly, the compounds of the present invention show relatively greater activity at lower dosage rates when pre-emergent application is utilized.

When applied at an appropriate application rate, the compounds of formula A are relatively less toxic toward broadleaf crops, including cotton, soybeans, sugar beets and peanuts, than towards weeds. The compounds of formula A are therefore useful as selective herbicides in a broadleaf crop locus.

For general herbicidal as well as for selective herbicidal use of compounds of formula A, the amount to be applied to attain the desired effect will vary depending on the particular crop, if employed for selective use, and other standard variables such as the compound employed, mode of application, conditions of treatment and the like. The appropriate application rates can be determined by routine procedures by those skilled in the art, or by comparing the activity of the compounds of the invention with standards for which the application rate is known, e.g. in greenhouse tests. However, in general, satisfactory results are usually obtained when the compound is applied at a rate in the range of from about 0.03 to 5.0 kg/ha, preferably from about 0.5 to 4 kg/ha, and more particularly from about 1.0 to 3.0 kg/ha, the application being repeated as necessary.

The compounds of formula A may be and preferably are employed as herbicidal compositions in association with agriculturally acceptable diluent(s). Suitable formulations contain from 0.01% to 99% by weight of active ingredient, from 0 to 20% surfactant and from 1 to 99.99% solid or liquid diluent(s). Higher ratios of surfactant to active ingredient are sometimes desirable and are achieved by incorporation into the formulation or by tank mixing. Application forms of a composition generally contain between 0.01 and 25% by weight of active ingredient. Lower or higher levels of active ingredient can, of course, be present depending on the intended use, the physical properties of the compound and the mode of application. Concentrate forms of a composition intended to be diluted before use generally contain between 2 and 90%, preferably between 10 and 82% by weight of active ingredient.

Useful formulations of the compounds of formula A include dusts, granules, suspension concentrates, wettable powders, emulsifiable concentrates, flowables and the like. They are obtained by conventional manner, e.g. by mixing a compound of formula A with the diluent(s) and optionally with other ingredients.

Alternatively, the compounds of formula A may be used in micro-encapsulated form.

Agriculturally acceptable additives may be employed in the herbicidal compositions to improve the performance of the active ingredient and to reduce foaming, caking and corrosion, for example.

"Surfactant" as used herein means an agriculturally acceptable material which imparts emulsifiability, spreading, wetting, dispersibility or other surface-modifying properties. Examples of surfactants are sodium lignin sulphonate and lauryl sulphate.

"Diluent" as used herein means a liquid or solid agriculturally acceptable material used to dilute a concentrated material to a usable or desirable strength. For dusts or granules it can be e.g. talc, kaolin or diatomaceous earth, for liquid concentrate forms for example a hydrocarbon such as xylene or an alcohol such as isopropanol, and for liquid application forms i.e. water or diesel oil.

The compositions of this invention can also comprise other compounds having biological activity, e.g. compounds having similar or complementary herbicidal activity or compounds having antidotal, fungicidal or insecticidal activity.

Specific non-limiting Examples of herbicidal compositions will now be described. Parts are percent by weight.

EXAMPLE A: Flowable 0.6 Parts of colloidal magnesium aluminium silicate (VEEGUM ®) is dispersed in 41.3 parts of water. 52.0 Parts of a compound of formula A, 6.0 parts of purified calcium lignin sulfonate (MARASPERSE ® C21) and 0.1 part of acetylenic glycol blend in propylene glycol (SURFYNOL ® TGE) are added, and the mixture is wet-milled until a medium particle size of 3–4 microns is obtained.

EXAMPLE B: Wettable Powder 82.0 Parts of a compound of formula A are mixed and milled with sodium lignin sulfonate (POLYFON ® H), 1.0 part of sodium dialkylnaphthalene sulfonate (SELLOGEN ® HR) and 13.0 parts of kaolin.

The following examples are provided to illustrate the practice of the present invention. Temperature is given in degrees centigrade. "RT" means room temperature.

FINAL COMPOUNDS

EXAMPLE 1

N-methyl-N-(2,3-dichlorophenyl)-2-pyridinesulfonamide 1-oxide

N-methyl-N-(2,3-dichlorophenyl)-2-pyridinesulfonamide (1.7 g, 5.3 mmol) is treated with 40% peracetic acid (approx. 12 ml) at 35°–45° under $N_2$ for 14 hours. The excess peracetic acid is removed under vacuum, and the residue is diluted with methylene chloride, poured into water, neutralized with aq. sodium bicarbonate, washed with brine, dried and evaporated to dryness to give, after purification, the title compound (compound 1, Table A).

nmr ($CDCl_3$) τ 6.37 (s, 3H), 2.63 (m, 5H), 2.15 (dd, 1H) and 1.69 ppm (dd, 1H).

EXAMPLE 2

Following the procedure of Example 1, each of the 2-pyridinesulfonamide 1-oxides of formula A″ under Table A is prepared.

TABLE A (A″)

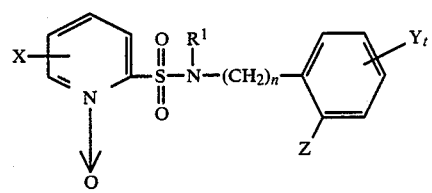

| Cpd | X | R¹ | n | Z | t | Y | MS (M⁺ + 1) | m.p. (°C.) |
|---|---|---|---|---|---|---|---|---|
| 1 | H | $CH_3$ | 0 | Cl | 1 | 3-Cl | 333.00 | 168 |
| 2 | H | $CH_3$ | 0 | Cl | 1 | 4-Cl | 334.00 | 192 |
| 3 | H | $CH_3$ | 0 | Cl | 0 | — | 299.00 | 192.5 |
| 4 | H | $CH_3$ | 0 | F | 0 | — | 282.00 | 161.5 |
| 5 | H | $CH_3$ | 0 | H | 0 | — | 265.05 | 138 |
| 6 | H | $CH_3$ | 0 | $CH_3$ | 1 | 5-$CH_3$ | 293.00 | 133 |
| 7 | H | $CH_3$ | 0 | H | 1 | 3-$CF_3$ | 333.15 | 142 |
| 8 | H | $CH_3$ | 1 | H | 1 | 4-Cl | 313.00 | 117.5 |
| 9 | H | $CH_3$ | 1 | Cl | 0 | — | 312.60 | 188.5 |
| 10 | H | $CH_2CH_3$ | 1 | Cl | 0 | — | 326.60 | 108 |
| 11 | H | $CH_2CH_3$ | 1 | H | 0 | — | 292.00 | 89 |
| 12 | H | $CH_3$ | 0 | $CF_3$ | 0 | — | 332.00 | 182 |

TABLE A-continued (A'')

$$\text{X}-\underset{\underset{\underset{O^-}{N^+}}{\parallel}}{\overset{O}{\underset{\parallel}{\text{S}}}}-\underset{\underset{Z}{}}{\text{N}}\underset{R^1}{}-(CH_2)_n-\text{C}_6\text{H}_3(Y)_t(Z)$$

| Cpd | X | $R^1$ | n | Z | t | Y | MS ($M^+ + 1$) | m.p. (°C.) |
|---|---|---|---|---|---|---|---|---|
| 13 | H | $CH_3$ | 0 | H | 1 | 4-Cl | 299.00 | 84 |
| 14 | H | $CH_3$ | 0 | H | 1 | 3-Cl | 299.00 | 148.5 |
| 15 | H | $CH_3$ | 0 | Cl | 1 | 5-Cl | 333.00 | 183.5 |
| 16 | H | $CH_3$ | 0 | H | 2 | 3,4-diCl | 334.90 | 113 |
| 17 | H | $CH_3$ | 0 | H | 2 | 3,5-diCl | 334.00 | 164 |
| 18 | H | $CH_3$ | 0 | Cl | 2 | 3,4-diCl | 368.95 | 183 |
| 19 | H | $CH_3$ | 0 | Cl | 2 | 4,6-diCl | 368.95 | 193 |
| 20 | H | $CH_3$ | 0 | $CH_3$ | 0 | — | 279.05 | 194 |
| 21 | H | $CH_3$ | 0 | $CH_3$ | 1 | 6-$CH_3$ | 293.15 | 187 |
| 22 | H | $CH_3$ | 0 | $CH_3$ | 1 | 6-Cl | 313.05 | 176 |
| 23 | H | $CH_3$ | 0 | $CH_3$ | 1 | 5-Cl | 313.05 | 169 |
| 24 | H | $CH_3$ | 0 | $CH_3$ | 1 | 5-F | 313.05 | 205 |
| 25 | H | $CH_3$ | 0 | Cl | 1 | 5-$CH_3$ | 297.15 | 175 |
| 26 | H | $CH_3$ | 0 | Cl | 1 | 5-$NO_2$ | 344.95 | 171 |
| 27 | H | $CH_3$ | 0 | Cl | 1 | 5-$CF_3$ | 367.90 | 156 |
| 28 | H | $CH_3$ | 0 | $CF_3$ | 1 | 4-Cl | 367.00 | 153.5 |
| 29 | H | $CH_3$ | 0 | $OCHF_2$ | 0 | — | 331.00 | 116 |
| 30 | H | $CH_3$ | 0 | $OCHF_2$ | 1 | 5-$CH_3$ | 345.15 | 108 |
| 31 | H | $CH_3$ | 0 | $OCHF_2$ | 1 | 5-Cl | 364.70 | 95 |
| 32 | H | $CH_3$ | 0 | $OCHF_2$ | 1 | 3-Cl | 364.70 | 137.5 |
| 33 | H | $CH_3$ | 1 | H | 0 | — | | |
| 34 | H | $CH_2CH_3$ | 0 | Cl | 1 | 5-Cl | 348.00 | 161 |
| 35 | H | $CH_2CH_3$ | 0 | $CF_3$ | 0 | — | 347.95 | 186.5 |
| 36 | H | $CH_2OCH_3$ | 0 | $CF_3$ | 0 | — | 363.00 | 127.5 |
| 37 | H | $CH_2CH=CH_2$ | 0 | $CF_3$ | 0 | — | 359.20 | 151.5 |
| 38 | H | $CH_2C(Cl)=CH_2$ | 0 | $CF_3$ | 0 | — | 393.05 | 148 |
| 39 | H | $CH_2C\equiv CH$ | 0 | $CF_3$ | 0 | — | 357.00 | 168 |
| 40 | H | $CH_2C(CH_3)=CH_2$ | 0 | $CF_3$ | 0 | — | 373.20 | 161 |
| 41 | H | $CH_2CH=CF_2$ | 0 | $CF_3$ | 0 | — | 394.00 | 99 |
| 42 | 5-Cl | $CH_3$ | 0 | $NO_2$ | 0 | — | 344.00 | 166 |
| 43 | 5-Cl | $CH_3$ | 0 | CN | 0 | — | 324.00 | 201.5 |
| 44 | H | $CH_3$ | 0 | CN | 0 | — | 290.00 | 176 |
| 45 | 5-Cl | $CH_3$ | 0 | $CF_3$ | 0 | — | 366.70 | 167 |
| 46 | 5-Cl | $CH_3$ | 0 | $OCHF_2$ | 1 | 5-$CH_3$ | 378.70 | 123 |
| 47 | 5-Cl | $CH_3$ | 0 | $OCHF_2$ | 1 | 5-Cl | 399.00 | 180.5 |
| 48 | 5-Cl | $CH_3$ | 0 | $OCHF_2$ | 0 | — | 364.70 | 132 |
| 49 | 5-$CF_3$ | $CH_3$ | 0 | $OCHF_2$ | 0 | — | 398.00 | 104.5 |
| 50 | 5-$CF_3$ | $CH_3$ | 0 | $OCHF_2$ | 1 | 5-$CH_3$ | | |
| 51 | 5-$CF_3$ | $CH_3$ | 0 | $OCHF_2$ | 1 | 5-Cl | | |
| 52 | 5-$CF_3$ | $CH_3$ | 0 | $CF_3$ | 0 | — | 400.00 | 165 |
| 53 | 4-$CH_3$ | $CH_3$ | 0 | Cl | 1 | 3-Cl | 348.95 | 175 |
| 54 | 4-$CH_3$ | $CH_3$ | 0 | Cl | 1 | 5-Cl | 347.00 | 204.5 |
| 55 | 5-$CH_3$ | $CH_3$ | 0 | $OCHF_2$ | 0 | — | 345.00 | 148.5 |
| 56 | 4-$CH_3$ | $CH_3$ | 0 | $OCHF_2$ | 1 | 5-Cl | | |
| 57 | 4-$CH_3$ | $CH_3$ | 0 | $CF_3$ | 0 | — | 347.05 | 201.5 |
| 58 | 3-$CH_3$ | $CH_3$ | 0 | Cl | 1 | 5-Cl | 348.00 | 190 |
| 59 | 3-$CH_3$ | $CH_3$ | 0 | $OCHF_2$ | 0 | — | | |
| 60 | 3-$CH_3$ | $CH_3$ | 0 | $OCHF_2$ | 1 | 5-Cl | | |
| 61 | 3-$CH_3$ | $CH_3$ | 0 | $CF_3$ | 0 | — | 347.05 | 188.5 |
| 62 | 5-Cl | $CH_2CH_3$ | 0 | $CF_3$ | 0 | — | 380.70 | 187 |
| 63 | 5-Cl | $CH_2CH=CH_2$ | 0 | $CF_3$ | 0 | — | 392.70 | 177.5 |
| 64 | 5-Cl | $CH_3$ | 0 | $OCHF_2$ | 1 | 3-Cl | 399.00 | 163 |
| 65 | 5-Cl | $CH_3$ | 0 | Cl | 1 | 3-Cl | 367.80 | 180 |
| 66 | 3-Cl | $CH_3$ | 0 | $CF_3$ | 0 | — | 366.70 | 210 |
| 67 | 4-Cl | $CH_3$ | 0 | $CF_3$ | 0 | — | 367.00 | 171 |
| 68 | 6-Cl | $CH_3$ | 0 | $CF_3$ | 0 | — | 367.00 | 159 |
| 69 | 4-Br | $CH_3$ | 0 | $CF_3$ | 0 | — | | |
| 70 | 5-Br | $CH_3$ | 0 | $CF_3$ | 0 | — | 413.00 | 187.5 |
| 71 | 6-Br | $CH_3$ | 0 | $CF_3$ | 0 | — | | |
| 72 | 4-F | $CH_3$ | 0 | $CF_3$ | 0 | — | | |
| 73 | 5-F | $CH_3$ | 0 | $CF_3$ | 0 | — | | |
| 74 | 6-F | $CH_3$ | 0 | $CF_3$ | 0 | — | | |
| 75 | 5-$CH_3$ | $CH_3$ | 0 | $CF_3$ | 0 | — | 347.00 | 176 |
| 76 | 6-$CH_3$ | $CH_3$ | 0 | $CF_3$ | 0 | — | 347.00 | 166.5 |
| 77 | H | $CH_3$ | 0 | $NO_2$ | 0 | — | 309.00 | 236 |
| 78 | H | $CH_3$ | 0 | $OCH_2CF_3$ | 0 | — | 363.00 | 87 |
| 79 | H | $CH_3$ | 0 | $OCH_2CF_3$ | 1 | 5-$CH_3$ | 377.00 | 108 |
| 80 | H | $CH_3$ | 0 | $OCH_2CF_3$ | 1 | 5-Cl | 397.00 | 148 |
| 81 | 5-Cl | $CH_3$ | 0 | $OCH_2CF_3$ | 0 | — | 397.00 | 149 |
| 82 | 5-Cl | $CH_3$ | 0 | $OCH_2CF_3$ | 1 | 5-$CH_3$ | 419.00 | 111 |

TABLE A-continued

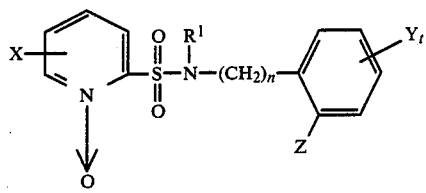

(A″)

| Cpd | X | R¹ | n | Z | t | Y | MS (M⁺ + 1) | m.p. (°C.) |
|---|---|---|---|---|---|---|---|---|
| 83 | 5-Cl | CH₃ | 0 | OCH₂CF₃ | 1 | 5-Cl | 431.00 | 164 |
| 84 | 5-Cl | CH₃ | 0 | OCH₂CF₃ | 1 | 5-CF₃ | 365.00 | 136 |
| 85 | 5-Cl | CH₃ | 0 | Cl | 1 | 5-Cl | 367.00 | 179.5 |
| 86 | 5-Cl | CH₃ | 0 | CF₃ | 1 | 5-Cl | | |
| 87 | 5-Cl | CH₃ | 0 | Cl | 1 | 5-CH₃ | 348.00 | 168.5 |
| 88 | 5-Cl | CH₃ | 0 | CH₃ | 1 | 3-Cl | 348.00 | 150 |
| 89 | 5-Cl | CH₃ | 0 | CH₃ | 1 | 5-Cl | 348.00 | 154.5 |
| 90 | 5-Cl | CH₃ | 0 | CH₃ | 0 | — | 313.00 | 175 |
| 91 | 5-Cl | CH₃ | 0 | CH₂CH₃ | 0 | — | 327.00 | 167 |
| 92 | 5-Cl | CH₃ | 0 | CH₂CH₃ | 1 | 6-CH₂CH₃ | 355.00 | 119 |
| 93 | 5-Cl | CH₃ | 0 | CH(CH₃)₂ | 0 | — | 341.00 | 155 |
| 94 | 5-Cl | CH₃ | 0 | H | 1 | 3-OCHF₂ | 365.00 | 80 |
| 95 | 5-Cl | CH₃ | 0 | OCHF₂ | 1 | 5-F | 383.00 | 145 |
| 96 | 5-Cl | CH₃ | 0 | OCF₂CHF₂ | 0 | — | 415.00 | 170 |
| 97 | 5-Cl | CH₃ | 0 | OCF₂CHClF | 0 | — | 432.00 | 152.5 |
| 98 | 5-Cl | CH₃ | 0 | Cl | 1 | 5-CF₃ | 402.00 | 134 |
| 99 | 5-Cl | CH₃ | 0 | F | 1 | 6-F | 335.00 | 171 |
| 100 | 5-Cl | CH₃ | 0 | F | 1 | 3-F | 335.00 | 163 |
| 101 | 5-Cl | CH₃ | 0 | F | 1 | 5-F | 335.00 | 152 |
| 102 | 5-Cl | CH₃ | 0 | F | 1 | 5-CF₃ | 385.00 | 106.5 |
| 103 | 5-Cl | CH₃ | 0 | F | 1 | 6-Cl | 351.00 | 189 |
| 104 | 5-Cl | CH₃ | 0 | CN | 1 | 3-Cl | 359.00 | 225 |
| 105 | 5-Cl | CH₃ | 0 | H | 1 | 3-Cl | 334.00 | 119 |
| 106 | 5-Cl | CH₃ | 0 | H | 1 | 4-CH₃ | 313.00 | 144.5 |
| 107 | 5-Cl | CH₃ | 0 | C(O)OCH₃ | 0 | — | 357.00 | 175 |
| 108 | 5-Cl | CH₃ | 0 | C(O)OCH₃ | 1 | 5-Cl | 391.00 | 146 |
| 109 | H | CH₃ | 0 | Cl | 1 | 6-F | 317.00 | 197 |
| 110 | H | CH₃ | 0 | F | 1 | 6-F | 301.00 | 157 |
| 111 | H | CH₃ | 0 | C(O)OCH₂CH₃ | 0 | — | 337.00 | 124.5 |
| 112 | H | CH₃ | 0 | C(O)OCH₃ | 1 | 5-Cl | 357.00 | 148.5 |
| 113 | H | CH(CH₃)₂ | 0 | CF₃ | 0 | — | 361.00 | 221 |
| 114 | H | CH₂CH₂CH₃ | 0 | CF₃ | 0 | — | 361.00 | 175 |
| 115 | H | CH₂CH₂CH₂CH₃ | 0 | CF₃ | 0 | — | 375.00 | 139 |
| 116 | 5-Cl | CH₂CH₂CH₃ | 0 | CF₃ | 0 | — | 395.00 | 164.5 |
| 117 | 5-Cl | CH₂CH₂CH₂CH₃ | 0 | CF₃ | 0 | — | 409.00 | 177 |
| 118 | 5-Cl | CH₃ | 0 | CH₂CH₃ | 1 | 5-Cl | 362.00 | 190 |
| 119 | 5-Cl | CH₂CH₃ | 0 | OCH₂CF₃ | 0 | — | 411.00 | 131 |
| 120 | 5-Cl | CH₂CH₃ | 0 | F | 1 | 6-F | 349.00 | 143.5 |
| 121 | 5-Cl | CH₂CH₃ | 0 | F | 1 | 6-Cl | 365.00 | 162 |
| 122 | 5-Cl | CH₂CH₃ | 0 | OCHF₂ | 0 | — | 379.00 | 149 |
| 123 | 5-Cl | CH₂CH₃ | 0 | OCHF₂ | 1 | 3-Cl | 414.00 | 202 |
| 124 | 5-Cl | CH₂CH₃ | 0 | OCHF₂ | 1 | 5-F | 397.00 | 130 |
| 125 | 5-Cl | CH₂CH₂CH₃ | 0 | F | 1 | 6-F | 363.00 | 120 |
| 126 | 5-Cl | CH₂CH₂CH₃ | 0 | F | 1 | 6-Cl | 379.00 | 151.5 |
| 127 | 5-Cl | CH₂CH₂CH₃ | 0 | OCHF₂ | 0 | — | 393.00 | 118 |
| 128 | 5-Cl | CH₃ | 0 | F | 3 | 3,5,6-triF | 371.00 | 146.5 |
| 129 | H | H | 0 | CF₃ | 0 | — | | |
| 130 | 5-Cl | CH₃ | 0 | Br | 1 | 6-Cl | 413.00 | 212 |
| 131 | 5-Cl | CH₃ | 0 | Br | 1 | 6-F | 396.00 | 183 |
| 132 | 5-Cl | CH₃ | 0 | Cl | 1 | 5-CH₂CH₃ | 362.00 | 140 |
| 133 | 5-Cl | CH₃ | 0 | Br | 0 | — | 378.00 | 184 |
| 134 | 5-Cl | CH₃ | 0 | CH₃ | 1 | 3-NO₂ | 358.00 | 156 |
| 135 | 5-Cl | CH₃ | 0 | NO₂ | 1 | 6CH₃ | 358.00 | 167 |
| 136 | 5-F | CH₃ | 0 | OCHF₂ | 0 | — | | |
| 137 | 5-F | CH₃ | 0 | OCH₂CF₃ | 0 | — | | |
| 138 | 5-F | CH₃ | 0 | F | 1 | 6-F | | |
| 139 | 5-F | CH₃ | 0 | F | 1 | 6-Cl | | |

EXAMPLE 3

N-allyl-N-(2-trifluoromethylphenyl)-2-pyridinesulfonamide 1-oxide

To N-(2-trifluoromethylphenyl)-2-pyridinesulfonamide 1-oxide (compound 129, Table A) (1.0 g, 3.0 mmol) in 10 ml of DMF is added NaH (0.30 g, 6.2 mmol) under N₂, and the mixture is stirred at RT for 30 minutes. Allyl bromide (0.82 g, 0.59 ml, 6.8 mmol) is added dropwise, and the mixture is stirred at RT for 48 hours. It is then worked up and purified to give the title compound (compound 37, Table A). (DMF is dimethylformamide; RT is room temperature.)

nmr (CDCl₃) 5.67–3.95 (m, 5H), 2.54 (m, 6H), 2.14 (dd, 1H, 8 Hz) and 1.64 ppm (dd, 1H, 8 Hz).

EXAMPLE 4

N-methyl-N-(3,5-dichloro-2-pyridyl)-2-pyridinesulfonamide 1-oxide

Following the procedures of Example 1, N-methyl-N-(3,5-dichloro-2-pyridyl)-2-pyridinesulfonamide is oxidized with 40% peracetic acid to give the title compound, MS m/e 334.00 (M+).

EXAMPLE 5

N-(2-chloro-3-pyridyl)-2-pyridinesulfonamide 1-oxide

Following the procedure of Example 1, 3-amino-2-chloropyridine (3.0 g, 24.0 mmol) is reacted with 2-pyridinesulfonyl chloride 1-oxide (24.0 mmol) to give the title compound.

EXAMPLE 6

N-methyl-N-(2-chloro-3-pyridyl)-2-pyridinesulfonamide 1-oxide

The title compound of Example 5 above is reacted with methyl iodide (0.6 g, 0.26 ml, 4.2 mmol) to give N-methyl-N-(2-chloro-3-pyridyl)-2-pyridinesulfonamide 1-oxide, MS m/e 300.00 (M+ +1).

BIOLOGICAL ACTIVITY

EXAMPLE 7

Pre-emergent herbicidal activity of compounds of the present invention of Formula A was determined as follows: Seeds of selected weeds were planted and the soil was drenched with a solution of the test compound (11.5 mg) in acetone (5.0 ml) and water (15.0 ml), at a rate equivalent to 10 lb/acre. Scoring was made two weeks after treatment. The grasses (GR) green foxtail, watergrass, shattercane and wild oats and the broadleafs (BL) annual morning glory, mustard, nightshade and velvetleaf were treated. The compounds of Formula A demonstrated herbicidal activity.

INTERMEDIATE COMpOUNDS

EXAMPLE 8

N-methyl-N-(2,3-dichlorophenyl)-2-pyridinesulfonamide

2-Pyridinesulfonyl chloride (46.0 mmol) is dissolved in cold methylene chloride and added dropwise at 0° to 2,3-dichloro-N-methylaniline (8.2 g, 46.0 mmol). The mixture is stirred at −10° for approx. 4 hours, then allowed to warm to RT. It is diluted with methylene chloride, washed with aqueous sodium bicarbonate and with brine, dried and evaporated to dryness to give, following purification, N-methyl-N-(2,3-dichlorophenyl)-2-pyridinesulfonamide.

What is claimed is:

1. A compound of the following formula (A):

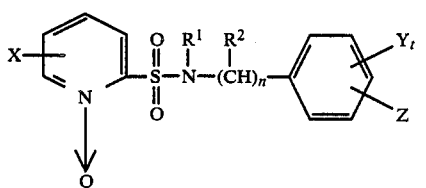

(A)

wherein, n is zero or one;

t is zero, one, two, three or four;

$R^1$ is hydrogen, unsubstituted or halogenated $C_{1-8}$alkyl, unsubstituted or halogenated $C_{2-8}$alkenyl, $C_{2-8}$alkynyl, $C_{2-10}$alkoxyalkyl or $C_{2-10}$alkylthioalkyl;

$R^2$ is hydrogen or $C_{1-8}$alkyl;

X is hydrogen, unsubstituted or halogenated $C_{1-8}$alkyl, $C_{1-8}$alkoxy, or halogen; and each of Y and Z is independently unsubstituted or halogenated $C_{1-8}$alkyl, unsubstituted or halogenated $C_{1-8}$alkoxy, $C_{1-8}$alkylthio, $C_{2-8}$alkoxycarbonyl, nitro, cyano or halogen.

2. A compound of the following formula, according to claim 1:

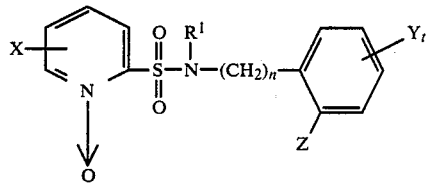

3. A compound according to claim 2 wherein n is zero; t is zero or one; $R^1$ is $C_{1-4}$alkyl, $C_{2-4}$alkenyl or $C_{2-4}$alkynyl; and X is hydrogen, methyl, chloro or fluoro.

4. A compound according to claim 3 wherein Y is methyl, chloro, fluoro, trifluoromethyl or nitro; and Z is methyl, chloro, fluoro, trifluoromethyl, difluoromethoxy or 2,2,2-trifluoroethoxy.

5. A compound according to claim 4 wherein t is zero and $R^1$ is methyl, ethyl, n-propyl, allyl or propargyl.

6. A compound according to claim 5 wherein Z is fluoro, trifluoromethyl, difluoromethoxy or 2,2,2-trifluoroethoxy.

7. A compound according to claim 6 wherein X is hydrogen, chloro or fluoro and is in the 3, 4 or 5 position.

8. The compound N-methyl-N-(2-trifluoromethylphenyl)-2-pyridinesulfonamide 1-oxide, according to claim 7.

9. The compound N-methyl-N-(2-trifluoromethylphenyl)-5-chloro-2-pyridinesulfonamide 1-oxide, according to claim 7.

10. The compound N-ethyl-N-(2-trifluoromethylphenyl)-2-pyridinesulfonamide 1-oxide, according to claim 7.

11. The compound N-ethyl-N-(2-trifluoromethylphenyl)-5-chloro-2-pyridinesulfonamide 1-oxide, according to claim 7.

12. The compound N-ethyl-N-(2-difluoromethoxyphenyl)-5-chloro-2-pyridinesulfonamide 1-oxide, according to claim 7.

13. The compound N-methyl-N-[2-(2,2,2-trifluoroethoxy)phenyl]-5-chloro-2-pyridinesulfonamide 1-oxide, according to claim 7.

14. A compound according to claim 4 wherein t is one and $R^1$ is methyl, ethyl, n-propyl, allyl or propargyl.

15. A compound according to claim 14 wherein X is hydrogen, chloro or fluoro and is in the 3, 4 or 5 position; and Y is chloro or fluoro and is in the 3, 5 or 6 position.

16. A compound according to claim 15 wherein Z is fluoro, trifluoromethyl, difluoromethoxy or 2,2,2-trifluoroethoxy.

17. The compound N-methyl-N-(2,5-difluorophenyl)-5-chloro-2-pyridinesulfonamide 1-oxide, according to claim 16.

18. The compound N-ethyl-N-(2,6-difluorophenyl)-5-chloro-2-pyridinesulfonamide 1-oxide, according to claim 16.

19. A method of combatting weeds which comprises applying to the weeds or the locus thereof a herbicidally effective amount of a compound of formula (A) as defined in claim 1.

* * * * *